(12) United States Patent
Seifert

(10) Patent No.: US 11,844,700 B2
(45) Date of Patent: Dec. 19, 2023

(54) INTERVERTEBRAL SPINAL IMPLANT

(71) Applicant: GLOBUS MEDICAL, INC., Audubon, PA (US)

(72) Inventor: Jody L. Seifert, Birdsboro, PA (US)

(73) Assignee: Globus Medical, Inc., Audubon, PA (US)

( * ) Notice: Subject to any disclaimer, the term of this patent is extended or adjusted under 35 U.S.C. 154(b) by 250 days.

(21) Appl. No.: 16/404,151

(22) Filed: May 6, 2019

(65) Prior Publication Data

US 2019/0254835 A1 Aug. 22, 2019

Related U.S. Application Data

(63) Continuation of application No. 15/489,948, filed on Apr. 18, 2017, now Pat. No. 10,322,008, which is a continuation of application No. 13/292,316, filed on Nov. 9, 2011, now Pat. No. 9,655,746.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3082* (2013.01); *A61F 2002/30266* (2013.01); *A61F 2002/30593* (2013.01); *A61F 2002/30774* (2013.01); *A61F 2002/30836* (2013.01); *A61F 2002/30841* (2013.01); *A61F 2002/30843* (2013.01); *A61F 2002/4622* (2013.01); *A61F 2002/4627* (2013.01); *A61F 2002/4629* (2013.01)

(58) Field of Classification Search
None
See application file for complete search history.

(56) References Cited

U.S. PATENT DOCUMENTS

| | | |
|---|---|---|
| 6,258,125 B1 | 7/2001 | Paul |
| 6,471,725 B1 | 10/2002 | Ralph |
| 6,964,687 B1 | 11/2005 | Bernard |
| 7,331,996 B2 | 12/2008 | Sato |
| 7,918,891 B1 | 4/2011 | Curran et al. |
| 8,252,060 B2* | 8/2012 | Hansell ................. A61F 2/4611 623/17.11 |
| 2006/0195190 A1 | 8/2006 | Lechmann |
| 2007/0027544 A1 | 2/2007 | Mccord |
| 2007/0050032 A1* | 3/2007 | Gittings ................. A61F 2/442 623/17.13 |

(Continued)

*Primary Examiner* — Jerrah Edwards
*Assistant Examiner* — Christine L Nelson

(57) ABSTRACT

An intervertebral implant for implantation in a treated area of an intervertebral space between vertebral bodies of a spine is provided. The upper surface and the lower surface of the implant each have a contact area capable of engaging with anatomy in the treated area, and the upper and lower surfaces define a through-hole having an inner surface extending through the spacer body. A first and second sidewalls extend from a front end and a back end, wherein the first and second sidewalls are configured with engagement portions positioned in close proximity to the front end and the back end. The front end and the back end are configured with a threaded hole for receiving an instrument for inserting the intervertebral implant into the intervertebral disc space.

14 Claims, 2 Drawing Sheets

(56) References Cited

U.S. PATENT DOCUMENTS

| | | | |
|---|---|---|---|
| 2007/0260320 A1* | 11/2007 | Peterman | A61F 2/447 623/17.16 |
| 2009/0105824 A1* | 4/2009 | Jones | A61F 2/447 623/17.16 |
| 2010/0228296 A1 | 9/2010 | Vraney | |
| 2010/0262249 A1 | 10/2010 | Peterman | |

* cited by examiner

INTERVERTEBRAL SPINAL IMPLANT

CROSS-REFERENCE TO RELATED APPLICATIONS

The present application is a continuation application of U.S. patent application Ser. No. 15/489,948, filed Apr. 18, 2017, which is a continuation application of U.S. patent application Ser. No. 13/292,316, filed Nov. 9, 2011, which is hereby incorporated by reference in its entirety.

FIELD OF THE INVENTION

The present disclosure generally relates to a fixation device for positioning and immobilizing at least two adjacent vertebrae. In particular, the present invention relates to an interbody fusion device for implementation in the spine.

BACKGROUND

The spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth. There is a need for an implant that can be inserted laterally into the vertebral disc space between adjacent vertebrae.

SUMMARY OF THE INVENTION

An intervertebral implant for implantation in a treated area of an intervertebral space between vertebral bodies of a spine is provided. The upper surface and the lower surface of the implant each have a contact area capable of engaging with anatomy in the treated area, and the upper and lower surfaces define a through-hole having an inner surface extending through the spacer body. A first and second sidewalls extend from a front end and a back end, wherein the first and second sidewalls are configured with engagement portions positioned in close proximity to the front end and the back end. The front end and the back end are configured with a threaded hole for receiving an instrument for inserting the intervertebral implant into the intervertebral disc space.

DETAILED DESCRIPTION OF THE ILLUSTRATED EMBODIMENTS

Embodiments of the disclosure are generally directed to an intervertebral implant for use with the anterior, anterolateral, lateral, and/or posterior portions of at least one motion segment unit of the spine. The systems of the invention are designed to be conformable to the spinal anatomy, so as to be generally less intrusive to surrounding tissue and vasculature than existing implants.

Figure 1:
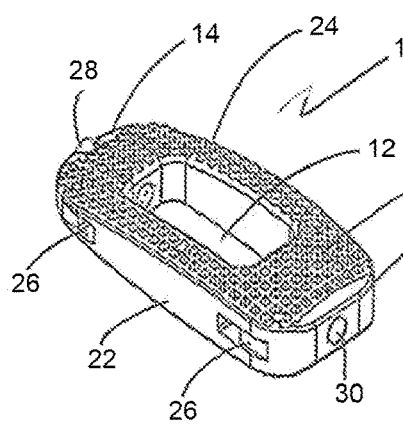
FIG. 1 is a perspective view of one embodiment of an intervertebral implant according to the present invention.
Figure 2:
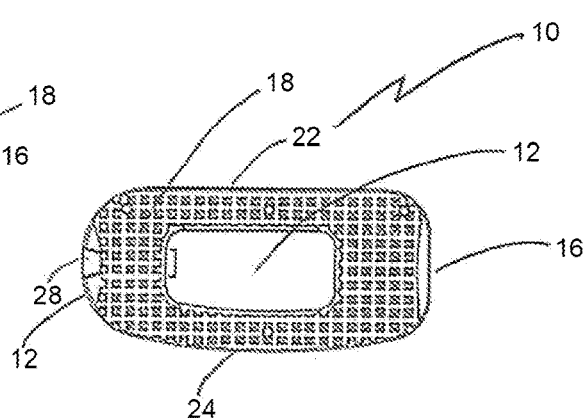
FIG. 2 is a top view of the intervertebral implant.
Figure 3:
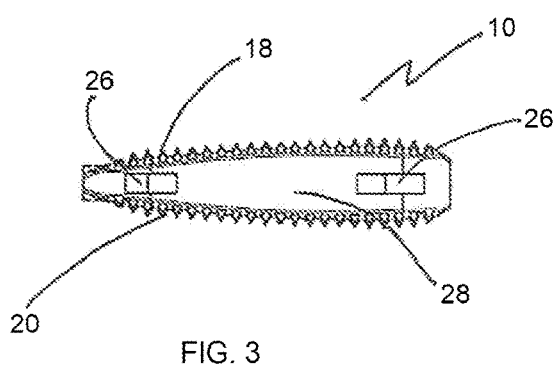
FIGS. 3 and 4 are side views of the intervertebral implant.
Figure 4:
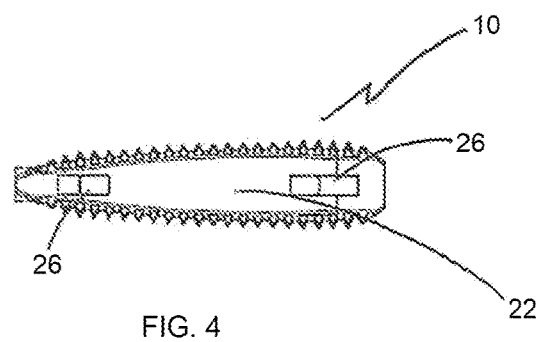
Figure 5:
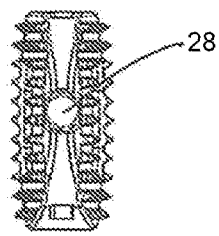
FIGS. 5 and 6 are front and back views of the intervertebral implant.
Figure 6:
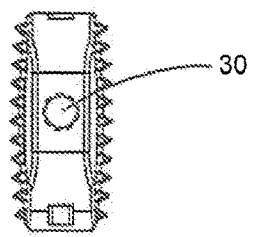

Referring now to FIGS. 1-6 one embodiment of a lateral intervertebral implant is shown. FIG. 1 is a perspective view of the implant according to the present invention. FIG. 2 illustrates a top view of the implant 10. As illustrated, the implant 10 is substantially rectangular with a hollow interior portion 12. The implant 10 is configured with a tapered front end 14 and a rectangular back end 16, as shown in FIGS. 3 and 4 which illustrate the side views of the implant 10. The implant 10 has an upper surface 18 and a parallel lower surface 20. The two side walls 22 and 24 are parallel to one another that extend from the back end 16 to the front end 14. The side walls 22 and 24 are configured with instrument attachment portions 26 near the front end 14 and the back end 16. The front end 14 and the back end 16 of the implant 10 are provided with a hole and/or aperture 28 and 30 for receiving an instrument that is used for inserting the implant 10. The implant 10 is coronally angled and allows for a surgeon to place the implant from the lateral approach regardless of the side of the access or direction of a scoliotic curve.

Figure 7:
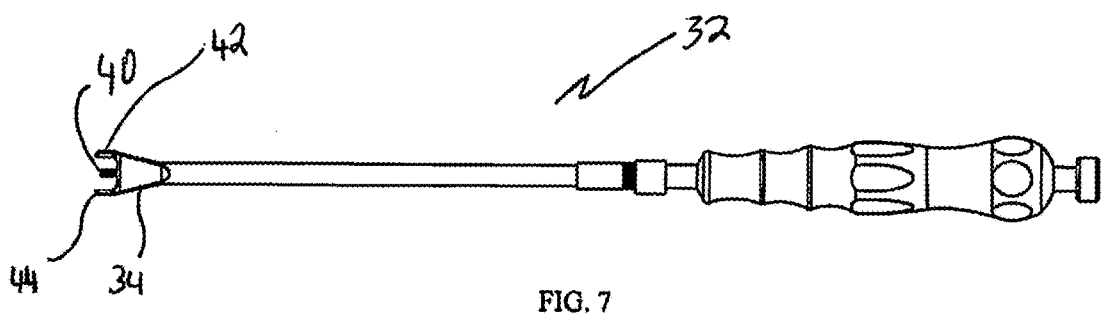
FIG. 7 is the instrument for engaging with the intervertebral implant during insertion.
Figure 8:
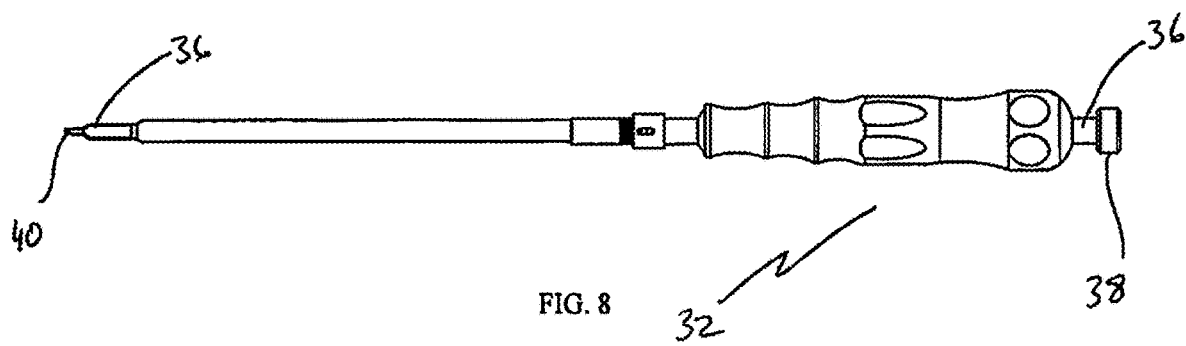
FIG. 8 is the threaded instrument for engaging with the intervertebral implant according to the present invention.

FIGS. 7 and 8 more clearly illustrates the instrument used for inserting the implant 10 into the intervertebral disc space. The instrument 32 comprises a substantially hollow tubular structure 34 having an internal rod 36 which is configured with a turning knob 38 at one end and a threaded portion 40 at the other end for threadeably engaging the threaded opening of the implant 10. The instrument 32 is configured with two extended arms 42 and 44 that engage with the attachment portions 26 of the implant. The implant is provided with attachment portions on the side walls of the front end and the back end so that the implant may be inserted in either direction. The internal rod 36 can be threaded into the back end of the implant or the front end depending on the surgeon's preference.

Bone graft and other bone material may be packed within the hollow portion of the implant which serves to promote bone ingrowth between the implant and the adjacent vertebrae. Once the bone ingrowth occurs, the implant will be a permanent fixture preventing dislodgement of the implant as well as preventing any movement between the adjacent vertebrae.

The implant 10 is also provided with a plurality of teeth projections extending form the upper and lower surfaces of the implant 10. Although the present implant illustrates teeth projections on the upper and lower surface, any type of projections may be utilized such as ridges. These projections prevent the implant from moving between the vertebrae, thus preventing movement of the implant prior to fusion.

Referring now to FIGS. 1-8, the method of inserting the implant 10 is described as follows. First, the threaded end of the internal rod of the instrument 32 is attached to the threaded opening of the implant by turning of the knob. Once the engaging end is in place, the extended arms 42 and 44 engage with attachment portions on the sidewalls of the implant. The implant is then placed at the entrance of the disc space between the two adjacent vertebrae. The knob is then tapped sufficiently hard enough the drive the implant into the disc space. It should be noted that the size of the implant is generally the same size as the disc space that is being replaced and can be either larger and/or smaller based on the intervertebral disc being removed.

While it is apparent that the invention disclosed herein is well calculated to fulfill the objects stated above, it will be appreciated that numerous modifications and embodiments may be devised by those skilled in the art.

What is claimed is:

1. A laterally approached spinal system for implantation in an intervertebral disc space between vertebral bodies of a spine, the system comprising:
    an insertion instrument, comprising:
        a threaded portion;
        a first extended arm; and
        a second extended arm, wherein the first extended arm and second extended arm are disposed laterally with respect to the threaded portion; and
    a laterally inserted implant configured to be attached to the insertion instrument, the implant comprising:
        a front tapered portion terminating at a front end having a front aperture;
        a back portion having upper and lower surfaces that are angled inwardly to define a back tapered portion and terminating at a back end having a back aperture, wherein the threaded portion of the insertion instrument is configured to thread into either the front aperture or the back aperture of the implant; and
        two side walls that extend from the back end to the front end, wherein the two side walls comprise engagement portions each spaced away from both the front end and the back end and are configured to receive the first and second extended arms of the insertion instrument;
    wherein the implant is coronally angled between the front tapered portion and the back tapered portion such that a height of the implant near the front tapered portion is lower than the height of the implant near the back tapered portion, and
    wherein the front portion and the back portion are each configured to be inserted into the intervertebral disc space such that the implant is insertable into the intervertebral space with the front portion or the back portion as a leading portion of insertion.

2. The system of claim 1, wherein the implant further comprises a hollow interior portion configured to receive graft material.

3. The system of claim 1, wherein the two side walls include a first side wall and a second side wall that extend between the front end and the back end, wherein the first side wall is straight and the second side wall is arched.

4. The system of claim 1, wherein the implant is configured to be inserted into the intervertebral disc space via a lateral approach.

5. The system of claim 4, wherein the implant comprises a hollow interior portion for receiving graft material.

6. The system of claim 4, wherein the two side walls include a first side wall and a second side wall that extends between the front end and the back end, wherein the first side wall is straight and the second side wall is convex.

7. The system of claim 1, wherein an upper surface and a lower surface of the implant includes teeth projections.

8. A laterally approached spinal system for implantation in an intervertebral disc space between vertebral bodies of a spine, the system comprising:
    an insertion instrument, comprising:
        a threaded portion,
        a first extended arm; and
        a second extended arm, wherein the first extended arm and second extended arm are disposed laterally with respect to the threaded portion; and
    a laterally inserted implant configured to be attached to the insertion instrument by threading the threaded portion into the implant and gripping the implant between the first extended arm and the second extended arm, the implant comprising:
        a front tapered portion terminating at a front end having a front aperture;
        a back portion having upper and lower surfaces that are angled inwardly to define a back tapered portion and terminating at a back end having a back aperture, wherein the threaded portion of the insertion instrument is configured to thread into either the front aperture or the back aperture of the implant; and
        a front end having a front aperture;
        a back end having a back aperture, wherein the threaded portion of the insertion instrument is configured to thread into either the front aperture or the back aperture of the implant; and
        two side walls that extend from the back end to the front end, wherein the two side walls comprise engagement portions each spaced away from both the front end and the back end and are configured to receive the first and second extended arms of the insertion instrument;
    wherein the implant is coronally angled such that a height of the implant near the front end is lower than the height of the implant near the back end, and
    wherein the front portion and the back portion are each configured to be inserted into the intervertebral disc space such that the implant is insertable into the intervertebral space with the front portion or the back portion as a leading portion of insertion.

9. The system of claim 8, wherein the implant comprises a hollow interior portion for receiving graft material.

10. The system of claim 8, wherein the implant comprises a tapered front end.

11. The system of claim 8, wherein the two side walls include a first side wall and a second side wall that extend between the front end and the back end, wherein the first side wall is straight and the second side wall is arched.

12. The system of claim 8, wherein delivering the implant comprises inserting the implant into the intervertebral disc space via a lateral approach.

13. The system of claim 12, wherein the implant comprises a hollow interior portion for receiving graft material.

14. The system of claim 12, wherein the two side walls include a first side wall and a second side wall that extends between the front end and the back end, wherein the first side wall is straight and the second side wall is convex.

\* \* \* \* \*